United States Patent [19]

Anapol et al.

[11] Patent Number: 5,128,193
[45] Date of Patent: Jul. 7, 1992

[54] ABSORBENT FIBROUS STRUCTURE

[75] Inventors: Sheryl J. Anapol; Hien V. Nguyen, both of East Windsor, N.J.

[73] Assignee: Chicopee, New Brunswick, N.J.

[21] Appl. No.: 754,150

[22] Filed: Sep. 4, 1991

Related U.S. Application Data

[63] Continuation of Ser. No. 625,579, Dec. 11, 1990, abandoned, which is a continuation-in-part of Ser. No. 595,736, Sep. 20, 1990, abandoned, which is a continuation of Ser. No. 465,044, Jan. 16, 1990, abandoned.

[51] Int. Cl.$^5$ ............................................. B32B 5/14
[52] U.S. Cl. .................................. 428/171; 156/209; 156/272.2; 428/170; 428/288; 428/296; 428/283; 428/913; 604/379
[58] Field of Search ............ 428/170, 171, 288, 296, 428/283, 913; 156/209, 272.2; 604/379

[56] References Cited

U.S. PATENT DOCUMENTS

| | | | |
|---|---|---|---|
| 2,905,568 | 9/1959 | Burgeni | 117/11 |
| 2,952,260 | 9/1960 | Burgeni | 128/290 |
| 3,017,304 | 1/1962 | Burgeni | 154/54 |
| 3,060,936 | 10/1962 | Burgeni | 128/290 |
| 3,065,751 | 11/1962 | Gobbo et al. | 123/287 |
| 3,766,922 | 10/1973 | Kruska | 128/284 |
| 3,886,941 | 6/1975 | Duane et al. | 128/287 |
| 3,993,820 | 11/1976 | Repke | 428/167 |
| 4,027,672 | 6/1977 | Karami | 128/284 |
| 4,443,512 | 4/1984 | Delvaux | 428/162 |

FOREIGN PATENT DOCUMENTS 974107 3/1971 Canada .
2061339 5/1981 United Kingdom .

Primary Examiner—James J. Bell
Attorney, Agent, or Firm—Lawrence D. Schuler

[57] ABSTRACT

A fibrous structure comprising a batt of a loose assemblage of fibers, having an initial density, that is embossed to produce a batt having a discrete pattern of hydrogen-bonded, compressed or densified portions and regions between the compressed portions. The regions have an average density greater than the average initial density of the batt and less than the density of the batt and less than the density of the compressed portions so as to form discrete density gradients across the surface of the batt. The batt has an initial average density of from about 0.03g/cm$^3$ to about 0.15 g/cm$^3$. The compressed portions have an average density in the range of from about 0.40 g/cm$^3$ to about 1.00 g/cm$^3$ and have a size in the range of from about 0.0002 cm$^2$ to about 0.12 cm$^2$. The regions defined between the compressed portions occupy from about 97 percent to about 99.5 percent of the area of the surface of the batt. The compressed portions may be formed by embossing rolls or by application of ultrasonic energy.

24 Claims, 2 Drawing Sheets

ABSORBENT FIBROUS STRUCTURE

This is a continuation of application Ser. No. 07/625,579, filed Dec. 11, 1990 now abandoned, which is a continuation-in-part of application Ser. No. 07/595,736, filed Sep. 20, 1990, now abandoned, which is a continuation of application Ser. No. 07/465,044, filed Jan. 16, 1990, now abandoned.

BACKGROUND OF THE INVENTION

1. Field of the Invention

The invention relates to an absorbent batt structure formed from a loose assemblage of fibers that has enhanced fluid transport and fluid distribution characteristics. More specifically, the invention relates to an absorbent batt formed from a loose assemblage of fibers that has a discrete pattern of bonded compressed portions formed on at least one surface of the batt.

2. Description of the Prior Art

Disposable absorbent articles, such as diapers, have been provided with absorbent batt structures to receive and retain body fluids. Such absorbent structures are normally made from an assemblage of fibers, such as comminuted wood pulp known as "fluff". In recent years such structures have been provided with superabsorbent materials to enhance the fluid holding capacity of the batts. In order for the articles to function in a suitable manner, the absorbent structures should be capable of transporting the body fluids from the point of discharge to remote areas of the structure; thus distributing the fluids throughout the structure and minimizing saturation at the point of discharge.

It is known to use absorbent structures in such articles that are compressed to a relatively high degree throughout the structure. The compression of such structures may be maintained by hydrogen bonds or adhesive bonds between adjacent fibers. Although such structures may transport the fluid throughout the structure, these structures are not completely satisfactory since the fluid transport capability is accompanied with a loss of total absorptive capacity. These structures are also relatively stiff and do not conform to the shape of an infant when used in a disposable diaper as readily as an uncompressed structure. However, absorbent structures that are relatively uncompressed throughout the structure are not capable of adequately distributing fluids in the structure. Thus, there is a trade off between distribution or wicking capacity and absorptive capacity and flexibility of these structures.

In an attempt to solve these problems, various solutions have been proposed that provide absorbent structures that are compressed to a reduced thickness in certain portions thereof to provide relatively dense and less dense portions of the structure. In theory, the compressed portions of the structures serve to distribute fluids to spaced portions of the structure, while the uncompressed portions of the structures serve to retain fluids. Examples of various embodiments of such absorbent structures are disclosed in issued U.S. patents as briefly discussed immediately hereinbelow.

U.S. Pat. Nos. 2,905,568; 2,952,260; and 3,017,304 to Burgeni disclose cellulosic fibrous batts with a paper-like densified layer or portions formed on at least one surface thereof. The densified layer or portions are formed by applying moisture and pressure at the surface of the batt. The densified portions comprise a relatively large portion of the surface of the batt.

U.S. Pat. No. 3,060,936 Burgeni discloses an absorbent product having a core of comminute wood pulp fibers attached to a cover and a backing sheet by moistening a surface of the core and subjecting the cover sheet, backing sheet and the core to compression to bond the components together. A patterned or intermittent compression is applied to the components to form a series of spaced-apart compressed portions separated by relatively uncompressed portions.

U.S. Pat. No. 3,993,820 to Repke discloses an absorbent product comprising a cellulosic fibrous batt having a densified, paper-like layer which, in selected portions, is thickened with additional densified cellulosic fibrous materials. The thickened or more densified portions may be intermittent or discontinuous lines formed in the batt. The area of each thickened or more densified intermittent portion appears to be materially greater than the area of the less densified portions of the batt.

U.S. Pat. No. 3,766,922 to Krusko discloses a disposable diaper product comprising a profiled, embossed fluff batt of cellulosic fibers. The embossed pattern defines compressed, densified valleys or circular islands and uncompressed ridges. The ratio of the area of compressed islands in the middle region of the product is approximately 6% of the middle region. The compressed islands are approximately one-fourth inch in diameter and are spaced apart on one and one-half inch centers in rows spaced by three-eights inch. The patent indicates that, by reducing the area of the compressed islands in the middle region, the fluid storing capacity is enhanced without adversely affecting the fluid wicking characteristics of the middle region.

U.S. Pat. No. 3,886,941 to Duane et al. discloses a diaper insert product comprising an absorbent pad disposed between a liquid impermeable hydrophobic top sheet and bottom sheet. The top and bottom sheets have a plurality of valvular opening (slits) formed therein. A plurality of spaced-apart dimples are formed in the top and bottom sheets which form compressed portions therebelow in the absorbent pad. The compressed portions cooperate with the valvular openings to close the openings as the compressed portions expand upon saturation. The total area of the dimples is disclosed as being between 4% to 12% of the area of the absorbent pad. The dimple size is disclosed as being in the range of about 0.025 to about 0.250 inch in diameter. The regions between the dimples appear to be uncompressed.

U.S. Pat. No. 4,027,672 to Karami discloses an absorbent pad having densified portions and undensified portions. The densified portions have a thickness at least as large as the thickness of the undensified portions.

U.S. Pat. No. 4,443,512 to Delvaux discloses an absorbent article comprising an absorbent pad that is embossed on either side or both sides so as to form relatively highly compressed portions while the other portions thereof are substantially not compressed. The discrete compressed portions are alleged to enhance liquid dispersion characteristics while reducing wetback. The size of the densified portions is in the range of 0.01 $cm^2$ to 2.0 $cm^2$. The distance between the densified portions is in the range of 0.1 cm to 3.0 cm. The density of the uncompressed pad is in the range of 0.06 $gm/cm^3$ to 0.12 $gm/cm^3$ and the density in the densified portions is in the range of 0.10 $gm/cm^3$ to 0.40 $gm/cm^3$. The densified portions occupy between 10% to 80% of the surface of the article.

U.S. Pat. No. 3,692,622 to Dunning discloses a paper product, useful in sanitary wipes and toweling applications, comprising an absorbent web structure of wood pulp fibers having a basis weight of 5 to 50 lbs./2880 sq. ft. The structure is provided with hydrogen bonded areas that are produced by application of moisture and pressure. The total bonded areas for the web structure is in the range of 5 percent to 40 percent and preferably in the range of 8 percent to 20 percent.

SUMMARY OF THE INVENTION

The present invention provides a fibrous absorbent structure that has enhanced fluid transport and fluid distribution characteristics with little, if any, sacrifice in absorbent capacity. The structure comprises a batt of a loose assemblage of fibers, having an initial average density, that is embossed to produce a batt having a discrete pattern of compressed or densified portions and regions between the compressed portions. The regions are slightly compressed and have an average density greater than the initial average density of the batt and substantially less than the average density of the compressed portions.

The term "average density" as used herein is intended to mean the density through the thickness of the batt or structure at selected points or areas of the surface of the batt or structure.

More specifically, in accordance with a presently considered preferred embodiment of the absorbent structure of the invention, the structure comprises a batt having opposing surfaces and formed from a loose assemblage of fibers including cellulosic fibers. The batt has an initial average density of from about 0.03 g/cm$^3$ to about 0.15 g/cm$^3$ (preferably of from about 0.05 g/cm$^3$ to about 0.10 g/cm$^3$). A plurality of spaced-apart, hydrogen-bonded, compressed portions are formed at least in one surface of the batt. The compressed portions have an average density in the range of from about 0.40 g/cm$^3$ to about 1.00 g/cm$^3$ and have a size in the range of from about 0.0002 cm$^2$ to about 0.12 cm$^2$ (preferably of from about 0.005 cm$^2$ to about 0.05 cm$^2$.

The batt has regions defined between the compressed portions that occupy from about 97 percent to about 99.5 percent of the area of the at least one surface of the batt. These regions have an average density throughout that is greater than the initial average density of the batt and less than the average density of the compressed portions so as to form discrete density gradients substantially uniformly across the surface of the batt and thereby enhance transfer of fluid between adjacent compressed portions while substantially maintaining the absorbency of the batt.

In accordance with presently preferred methods of the invention for making an absorbent structure having enhanced fluid transport and fluid distribution characteristics, a batt is formed having opposing surfaces from a loose assemblage of fibers including cellulosic fibers. The batt is formed to have an initial average density of from about 0.03 g/cm$^3$ to about 0.15 g/cm$^3$ (preferably of from about 0.05 g/cm$^2$ to about 0.10 g/cm$^3$). Water is sprayed on at least one surface of the batt and pressure, by an embossing roll or an alternative source of energy, is applied to the surface to define a plurality of substantially uniformly spaced-apart, hydrogen-bonded, compressed portions and unbonded regions between the compressed portions. The compressed portions are formed so as to have a size in the range of from about 0.0002 cm$^2$ to about 0.12 cm$^2$ (preferably of from about 0.005 cm$^2$ to about 0.05 cm$^2$) and an average density of from about 0.40 g/cm$^3$ to about 1.00 g/cm$^3$. The regions between the compressed portions are formed to occupy from about 97 percent to about 99.5 percent of the area of the surface and have an average density throughout that is greater than the initial average density of the batt and less than the average density of the compressed portions.

The compressed portions and the regions therebetween may be formed by rolling an embossing roll with a pattern of teeth across the sprayed surface of the batt. In so doing, a discrete pattern of hydrogen-bonded compressed portions are formed and the regions therebetween are compressed to a lesser extent. In accordance with preferred embodiments of the invention, the compressed portions may be embossed on either or both surfaces of the batt. In these embodiments both of the surfaces are sprayed with water and the embossing roll or rolls is passed over one surface at a time or over both surfaces at the same time. The direction of rolling can be the same or different for the two surfaces, for example one can be in the machine direction and the other in the cross-machine direction.

In accordance with another preferred embodiment of the invention, the compressed portions and the regions therebetween may be formed by applying ultrasonic energy to discrete locations in the batt by an ultrasonic horn in cooperation with a cylinder with a pattern of protruding pins. The water-sprayed batt is passed through a gap between the horn and the cylinder.

In accordance with other preferred embodiments of the invention, the batt may include superabsorbent materials to enhance the absorbent capacity of the structure and/or thermoplastic materials to permit fusion bonding of the fibers in the compressed portions.

DESCRIPTION OF THE PREFERRED EMBODIMENTS

Figure 1:
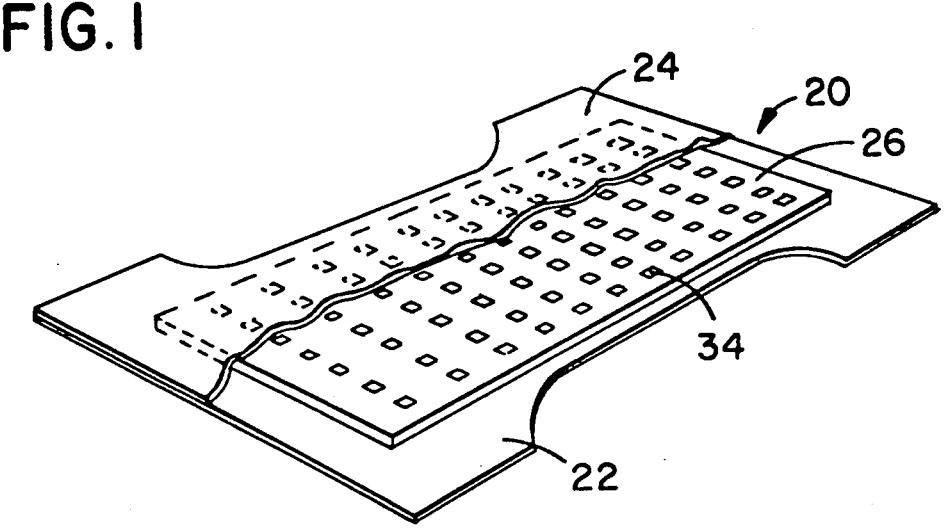
FIG. 1 is a cut-away view of a representative diaper of the type that may incorporate the absorbent batt structure of the invention.

While this invention is susceptible of embodiment in many different forms, there is shown in the drawings and will herein be described in detail certain preferred embodiments of the invention and modifications thereof, with the understanding that the present disclosure is to be considered as an exemplification of the principles of the invention and is not intended to limit the invention to the embodiments illustrated and described. Similar elements of these embodiments will be labelled and identified with the same reference numeral.

Although the absorbent batt structure of the present invention is useful for many purposes, such as sanitary pads, dressings, or the like, the article will be described in the form of an absorbent panel for a disposable diaper for convenience. Referring to FIG. 1, an exemplary diaper 20 is shown comprising a fluid impervious backing sheet 22 defining a back surface of the diaper, a fluid pervious top or cover sheet 24 defining a substantial portion of a front surface of the diaper, and an absorbent batt structure or panel 26 positioned between the backing sheet 22 and the top sheet 24. The diaper may have a pair of conventional tape fasteners (not shown) for use in securing the diaper about an infant during placement of the diaper.

Figure 2:
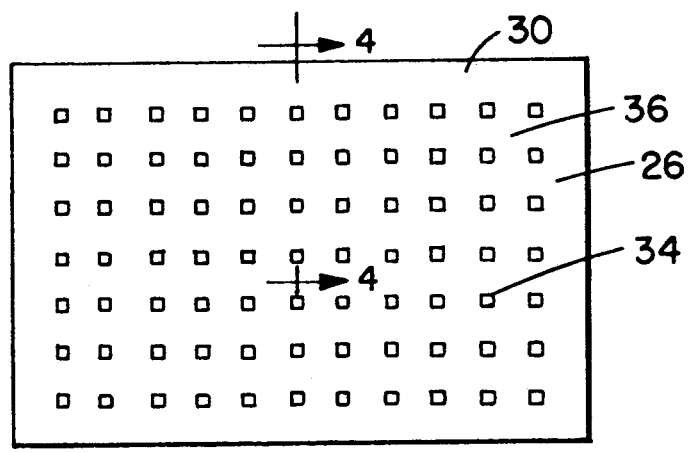
FIG. 2 is a top plan view of a portion of an absorbent batt structure in accordance with the invention.
Figure 3:
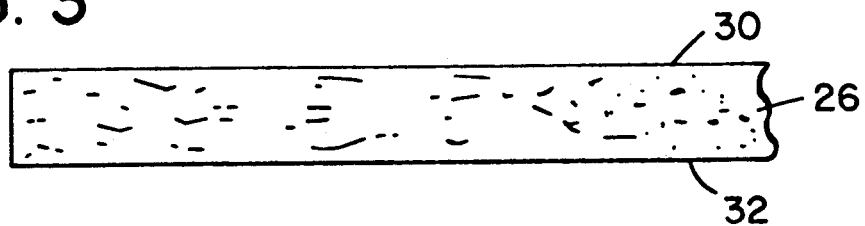
FIG. 3 is a sectional view taken through a portion of the initial fibrous batt prior to embossing.
Figure 4:
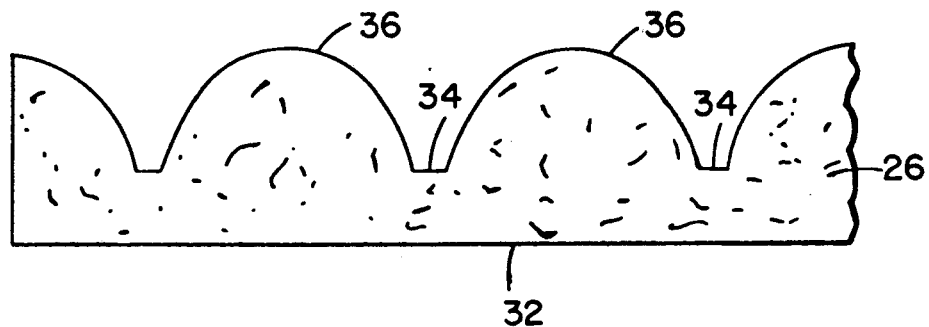
FIG. 4 is a sectional view of the batt in FIG. 3 after embossing of the top surface thereof in accordance with the invention.

In order for the diaper to function in a suitable manner, the absorbent batt structure or panel 26 should be capable of transporting the body fluids from the point of discharge to remote areas of the structure while maintaining a high absorbent capacity of the structure. Referring to FIGS. 2-4, the absorbent batt structure 26 comprises a loose assemblage of fibers defining a batt or web having opposing surfaces 30 and 32. Formed in one or both of the surfaces 30 and 32 of the batt is a discrete pattern of spaced-apart compressed or densified portions or spots 34 and regions 36 therebetween.

The structure 26 is formed of a loose assemblage of fibers, preferably cellulose fibers such as wood pulp fibers, or cotton linters, or mixtures thereof, which are primarily held together by interfiber bonds, requiring no added adhesive, as is well known in the art.

More specifically, it is preferable that the structure 26 be formed from an initial low bulk density coherent batt of loosely compacted comminuted wood pulp fibers in the form of so-called "fluff". The batt is formed from an assemblage of fibers having a basis weight of from about 2 oz/yd$^2$ to about 30 oz/yd$^2$ (preferably from about 4 oz/yd$^2$ to about 21 oz/yd$^2$) and has an initial average density of from about 0.03 g/cm$^3$ to about 0.15 g/cm$^3$ (preferably from about 0.05 g/cm$^3$ to about 0.10 g/cm$^3$.

At least one of the surfaces of the initial batt has a discrete pattern of substantially uniformly spaced apart compressed portions 34 and regions 36 therebetween formed thereon. The compressed portions 34 have an average density from about 0.40 g/cm$^3$ to about 1.00 g/cm$^3$ (preferably of from about 0.60 g/cm$^3$ to about 0.90 g/cm$^3$). The size of the compressed portion 34 is in the range of from about 0.0002 cm$^2$ to about 0.12 cm$^2$ (preferably of from about 0.005 cm$^2$ to about 0.05 cm$^2$). The compressed portions 34 may be of rectangular, round or other suitable shape. As will be discussed further hereinbelow, the surface of the batt is sprayed with water, so that hydrogen-bonds are formed at the compressed portions 34. The regions 36 occupy from about 97 percent to about 99.5 percent of the total area of the surface. The average density throughout the regions 36 is greater than the initial average density of the batt prior to compression and less than the average density of the compressed portions 34. In so doing discrete density gradients are imparted uniformly at points across the surface of the structure, as graphical represented in FIG. 6. The structure has superior fluid transport and enhanced fluid distribution with little, if any, sacrifice in absorbent capacity. The structure also has increased cohesive strength.

In accordance with a preferred method of the present invention, an absorbent structure 26 is made by forming a batt from a loose assemblage of cellulosic fibers having a basis weight of from about 2 oz/yd$^2$ to about 30 oz/yd$^2$ (preferably from about 4 oz/yd to about 21 oz/yd) in a well known manner. The batt as formed has an initial average density of from about 0.03 g/cm$^3$ to about 0.15 g/cm$^3$ (preferably of from about 0.05 g/cm$^3$ to about 0.10 g/cm$^3$). At least one of the surfaces 30, 32 of the batt is sprayed with approximately 15% (by weight) distilled water or an aqueous solution of salt, odor controlling agent, etc. A cylindrical embossing roll with a pattern of teeth, preferably wire-wound lickerins, is rolled across the sprayed surface 30, 32 of the batt at a sufficient pressure to form the discrete pattern of hydrogen-bonded compressed portions 34 and the regions 36 having size and density relationships as discussed hereinabove. The size and disposition of the teeth of the wires may be varied depending upon the particular pattern to be imparted to the surface.

Figure 5:
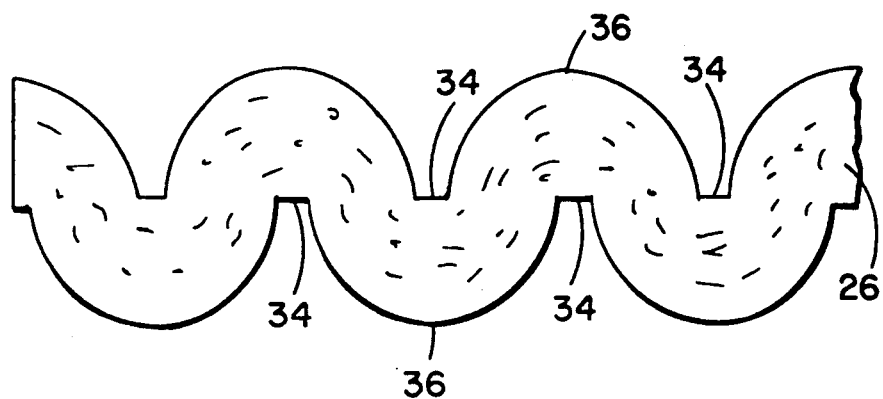
FIG. 5 is a view similar to FIG. 5 showing an alternative embodiment of the invention having embossing in accordance with the invention on both sides of the fibrous batt.

Referring to FIG. 5, in accordance with an alternative embodiment of the invention both of the surfaces 30, 32 are embossed substantially in the same manner as discussed above. In this embodiment both of the surfaces are sprayed with water or an aqueous solution and a toothed roller or rollers is passed over one surface at a time, or over both surfaces at the same time, to form the compressed portions 34 and the regions 36. The direction of rolling may be the same or different for the surfaces 30, 32 e.g., one can be in the machine direction and the other in the cross-machine direction. The direction of rolling may also be angular with respect to the machine direction.

In accordance with another preferred method of the present invention, at least one of the surfaces 30, 32 of the batt is sprayed as discussed above. The compressed portions 34 and the regions 36, having size and density relationships as discussed hereinabove, are formed by the application of ultrasonic energy to provide localized simultaneous compression and heating to form the compressed portions. The ultrasonic energy may be applied by known apparatus that includes a downwardly pointing ultrasonic horn and a motor-driven cylinder with a pattern of protruding pins positioned directly below the horn. The web is directed through a gap between the horn and the cylinder. The gap between the horn and the outer surface of the cylinder is adjusted so as to provide enough contact to the web so that the ultrasonic energy can be transferred efficiently into the web without applying too much pressure to the web. This results in the formation of a discrete pattern of densified hydrogen-bonded portions on the web. The density of the compressed portions 34 so formed tends to be greater in the center and less adjacent the edges thereof.

The web may be passed through the ultrasonic unit a second or more times to obtain superimposition of patterns. Different passes may use the same or different pin patterns. The faces of the web may also be reversed between passes.

In accordance with a further alternative embodiment of the invention, the batt may be formed with substantially water-insoluble hydrogel superabsorbent materials imparted therein to enhance the absorbency of the batt as is well known. The superabsorbent materials may be uniformly distributed throughout the batt or may be concentrated in specific selected areas. Examples of suitable superabsorbent materials include polyacrylamides, polyvinyl alcohol, ethylene maleic anhydride copolymers, polyvinyl ethers, hydroxypropyl cellulose, carboxymethyl cellulose, polyvinyl morpholinone, polymers and copolymers of vinyl sulfonic acid, polyacrylates, polyacrylamides, polyvinyl pyridine and the like. The superabsorbent materials are preferably in the range of from about 1.0 percent to 50 percent (by weight) of the batt (most preferably about 37 percent).

In accordance with a yet further alternative embodiment of the invention, the batt 26 may be formed with synthetic thermoplastic fibers or particles imparted therein. The thermoplastic fibers or particles may include polyethylene, polyester, nylon, cellulose acetate, and the like. The thermoplastic fibers or particles are preferably in the range of from about 10 to 50 percent (by weight) of the batt (most preferably about 24 percent). The compressed portions 34 may be formed by ultrasonic pin pointed fusion bonding of the thermoplastic fibers to each other and to the other fibers in a manner well known in the art. The fusion bonding of thermoplastic fibers when superabsorbent particles are present assists in preventing the superabsorbent particles from dusting out.

The absorbent structures of the present invention are further disclosed by the following examples and the discussion of certain tests that compare the wicking and fluid distribution performance of these examples with other absorbent structures. In particular, the performance of samples of the present invention are compared with the performance of three other samples; namely a control sample, a dry compressed control sample, and a sample with a continuous densified hydrogen-bonded skin of the type disclosed in U.S. Pat. No. 3,017,304 to Burgeni.

EXAMPLE I

Figure 6:
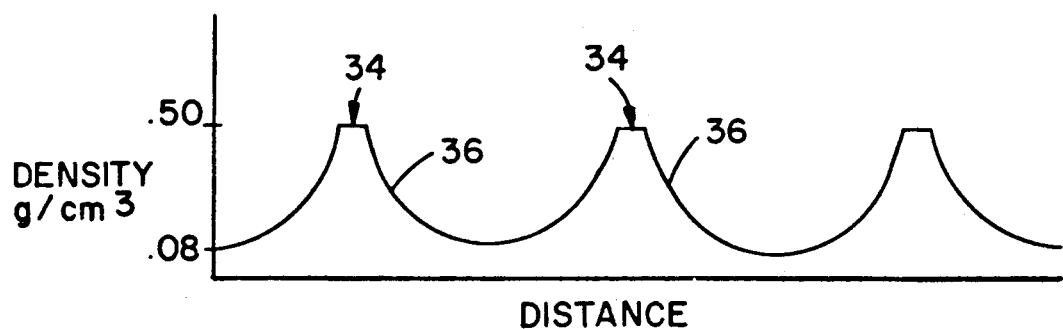
FIG. 6 is a graphical representation of the density gradient between adjacent compressed portions of an exemplanary absorbent batt structure of the invention.

Samples A, B, C and D are all made from a RAY FLOC J PULP batt (available from ITT Rayonair) having a weight of 4.0 oz/yd$^2$ and an initial average density of 0.07 g/cm$^3$. Sample A is a control sample having an average density of 0.07 g/cm$^3$. Sample B is a dry compressed control sample that is compressed to have an average density of 0.10 g/cm$^3$. Sample C is a sample with a continuous densified hydrogen-bonded skin having an average density of about 0.8 g/cm$^3$, as taught by U.S. Pat. No. 3,017,304. Sample D is a sample constructed in accordance with the present invention utilizing an embossing roller, wherein both surfaces are embossed so as to have a discrete pattern of rectangular compressed portions each having an area of about 0.01 cm$^2$. The total area of the compressed portions is approximately 2.3% of the total area of the surface. The area of the compressed portions is determined by placing on a flat table a white piece of paper with a carbon paper on top. The embossing roller used to emboss the surface is passed over the carbon paper leaving a pattern imprinted on the white paper. The imprint is enlarged on a photocopy machine a number of times so that the spots corresponding to the compressed portions are large enough to measure. The actual dimensions of each of the compressed portions is determined by dividing these measurements by the number of times the spots are enlarged and the area of each compressed portion calculated based on these dimensions. The percent of the total surface are occupied by the compressed portions is determined by adding up the total area of the compressed portions over a given surface area and dividing the number by the surface area. The compressed portions have an average density of about 0.7 g/cm$^3$. The regions have a density gradient between adjacent compressed portions of between about 0.08 g/cm$^3$ to about 0.50 g/cm$^3$, as shown in FIG. 6. The sample is embossed on one surface in the machine direction and on the other surface in the cross-machine direction. The average density of Sample D is about 0.10 g/cm$^3$.

Each of the samples is cut in the machine direction to a size of 21×6 cm. The longitudinal edges are teased off with a wire comb (0.5 cm each side) to inhibit wicking influenced by the increased density created along the cut edges. The samples are left to dry under TAPPI conditions and are marked in one centimeter intervals along the length thereof. The dry weights and the thickness of each sample is recorded. Each sample is inclined to 60 degrees and supported on a wire frame that is connected to a fluid source having absorption outputs connected to a strip chart recorder. Each sample is allowed to wick undisturbed for a period of thirty minutes while the strip chart records time versus fluid pick up. At the end of thirty minutes, fluid contact is broken and the sample is cut into segments along the one centimeter lines along the length of the sample. Each segment is weighed, placed in an oven to dry, and is then weighed again. Fluid distribution was determined from these weights.

The results of the tests are summarized in the following Tables I and II, wherein the wicking capacity is a gram/gram fluid capacity, based upon the entire weight of the sample versus time, and the fluid distribution is a gram/gram distribution of fluid capacity, based upon the location of that fluid after wicking for thirty minutes.

TABLE I

| Time (secs) | Wicking Capacity (g/g) vs Time | | | |
| --- | --- | --- | --- | --- |
| | Sample A | Sample B | Sample C | Sample D |
| 0 | 0.00 | 0.00 | 0.00 | 0.00 |
| 12 | 2.49 | 2.13 | 1.85 | 1.97 |
| 24 | 2.94 | 2.56 | 2.39 | 2.52 |
| 36 | 3.11 | 2.85 | 2.70 | 2.89 |
| 48 | 3.23 | 3.08 | 2.89 | 3.11 |
| 60 | 3.28 | 3.26 | 3.04 | 3.31 |
| 72 | 3.31 | 3.39 | 3.13 | 3.47 |
| 84 | 3.34 | 3.52 | 3.22 | 3.61 |
| 96 | 3.36 | 3.61 | 3.29 | 3.71 |
| 108 | 3.37 | 3.71 | 3.34 | 3.80 |
| 120 | 3.38 | 3.78 | 3.38 | 3.89 |
| 180 | 3.41 | 4.00 | 3.56 | 4.23 |
| 300 | 3.44 | 4.26 | 3.74 | 4.64 |
| 600 | 3.49 | 4.46 | 3.95 | 5.17 |
| 1200 | 3.58 | 4.70 | 4.14 | 5.65 |
| 1800 | 3.62 | 4.80 | 4.26 | 5.93 |

TABLE II

| cm | Fluid Distribution (g/g) | | | |
| --- | --- | --- | --- | --- |
| | Sample A | Sample B | Sample C | Sample D |
| 1 | 14.56 | 15.07 | 12.57 | 13.74 |
| 3 | 11.50 | 11.08 | 11.17 | 9.94 |
| 5 | 9.47 | 8.84 | 9.68 | 8.65 |
| 7 | 6.48 | 7.79 | 7.90 | 7.95 |
| 9 | 0.74 | 6.89 | 5.35 | 7.11 |
| 11 | 0.00 | 6.01 | 2.86 | 6.78 |
| 13 | 0.00 | 5.29 | 1.66 | 6.20 |
| 15 | 0.00 | 3.26 | 0.87 | 5.00 |
| 17 | 0.00 | 0.39 | 0.53 | 3.75 |
| 19 | 0.00 | 0.01 | 0.43 | 2.17 |
| 21 | 0.00 | 0.00 | 0.36 | 1.25 |

Surprisingly, it can be seen from the above test results that the absorbent structure in accordance with the present invention (Sample D) wicks further at a given time, has the highest wicking capacity and the most efficient liquid distribution.

EXAMPLE II

The same tests as set forth in Example I are conducted on Samples E, F, G and H. These samples are all made from a RAY FLOC J PULP (available from ITT Rayonair) batt having a weight of 12.0 oz/yd$^2$. Samples E and G are control samples respectively having an average density of 0.03 g/cm$^3$ and 0.08 g/cm$^3$. Sample F is constructed in the same manner as Sample D discussed above except that it is made from a batt having an initial average density 0.03 g/cm$^3$. The compressed portions have an average density of about 0.7 g/cm$^3$ and the regions have a density gradient between adjacent compressed portions of between 0.04 g/cm$^3$ to 0.60 g/cm$^3$. Sample H is also constructed in the same manner as Sample D discussed about except that it is made from a batt having an initial density of 0.08 g/cm$^3$. The compressed portions have an average density of 0.70 g/cm$^3$ and the regions have a density gradient between adjacent compressed portions of between 0.09 g/cm$^3$ to 0.60 g/cm$^3$.

The results of the tests on these samples are summarized in Tables III and IV as follows:

TABLE III

| | Wicking Capacity (g/g) vs Time | | | |
|---|---|---|---|---|
| Time (secs) | Sample A | Sample B | Sample C | Sample D |
| 0 | 0.00 | 0.00 | 0.00 | 0.00 |
| 12 | 1.06 | 1.30 | 1.80 | 1.09 |
| 24 | 1.47 | 2.04 | 2.70 | 1.97 |
| 36 | 1.78 | 2.52 | 3.25 | 2.47 |
| 48 | 1.94 | 2.83 | 3.60 | 2.86 |
| 60 | 2.04 | 3.07 | 3.85 | 3.16 |
| 72 | 2.13 | 3.27 | 4.03 | 3.42 |
| 84 | 2.18 | 3.34 | 4.16 | 3.61 |
| 96 | 2.23 | 3.54 | 4.26 | 3.78 |
| 108 | 2.28 | 3.65 | 4.35 | 3.93 |
| 120 | 2.33 | 3.73 | 4.41 | 4.07 |
| 180 | 2.45 | 4.03 | 4.63 | 4.61 |
| 300 | 2.58 | 4.39 | 4.83 | 5.25 |
| 600 | 2.70 | 4.80 | 5.01 | 5.80 |
| 1200 | 2.86 | 5.07 | 5.17 | 6.09 |
| 1800 | 3.03 | 5.22 | 5.27 | 6.24 |

TABLE IV

| | Fluid Distribution (g/g) | | | |
|---|---|---|---|---|
| cm | Sample A | Sample B | Sample C | Sample D |
| 1 | 20.56 | 13.76 | 16.67 | 12.84 |
| 3 | 14.52 | 11.28 | 11.29 | 10.66 |
| 5 | 11.12 | 9.72 | 9.72 | 9.04 |
| 7 | 4.20 | 8.38 | 8.73 | 8.46 |
| 9 | 0.19 | 4.91 | 7.94 | 7.66 |
| 11 | 0.00 | 3.54 | 5.44 | 5.88 |
| 13 | 0.00 | 2.98 | 2.20 | 4.11 |
| 15 | 0.00 | 2.32 | 0.17 | 3.64 |
| 17 | 0.00 | 1.86 | 0.00 | 2.65 |
| 19 | 0.00 | 1.68 | 0.00 | 2.32 |
| 21 | 0.00 | 1.30 | 0.00 | 1.66 |

It is significant to note that the Sample F and H constructed in accordance with the invention possessed greater absorption capacity, better fluid transport and more efficient distribution of the fluid than that of the respective corresponding Samples E and G.

EXAMPLE III

Sample I is made from a RAY FLOC J PULP batt (available from ITT Rayonair), having a basis weight of 4.0 oz/yd$^2$ and an initial average density of 0.7 g/cm$^3$, utilizing ultrasonic energy in accordance with the invention. The sample is made on an ultrasonic unit made by Branson Ultrasonics Corporation. The cylinder has a square pattern of pins of ⅛ inch in distance apart in the axial direction and ¼ inch apart in the circular direction. The traveling speed of the web driven by the cylinder is about 10 ft/min. Sample I is embossed on one of its surfaces so as to have a discrete pattern of rectangular compressed portions each having an area of about 0.005 cm$^2$. The total area of the compressed portions is approximately 1.4% of the total area of the surface. The compressed portions have a density gradient in range of about 0.5 g/cm$^3$ to about 1.0 g/cm$^3$ and an average density of about 0.7 g/cm$^3$. The regions have a density gradient between adjacent compressed portions of between about 0.08 g/cm$^3$ to about 0.50 g/cm$^3$.

The same tests as set forth in Example I is conducted on Sample I. The results of the tests on this sample is summarized in Tables V and VI as follows:

TABLE V

| Wicking Capacity (g/g) vs Time | |
|---|---|
| Time (secs) | Sample I |
| 0 | 0.00 |
| 12 | 1.94 |
| 24 | 2.50 |
| 36 | 2.86 |
| 48 | 3.06 |
| 60 | 3.27 |
| 72 | 3.41 |
| 84 | 3.55 |
| 96 | 3.69 |
| 108 | 3.79 |
| 120 | 3.87 |
| 180 | 4.21 |
| 300 | 4.69 |
| 600 | 5.40 |
| 1200 | 6.00 |
| 1800 | 6.35 |

TABLE VI

| Fluid Distribution (g/g) | |
|---|---|
| cm | Sample I |
| 1 | 10.00 |
| 3 | 6.80 |
| 5 | 6.06 |
| 7 | 5.67 |
| 9 | 5.41 |
| 11 | 5.12 |
| 13 | 4.80 |
| 15 | 4.59 |
| 17 | 4.14 |
| 19 | 3.38 |
| 21 | 2.61 |

It will be understood by those skilled in the art that variations and modifications of the specific embodiments described above may be employed without departing from the scope of the invention as defined in the appended claims.

What is claimed is:

1. An absorbent structure having improved fluid transport and fluid distribution characteristics, comprising: a batt having opposing surfaces and formed from a loose assemblage of fibers, said batt having a initial average density of from about 0.03 g/cm$^3$ to about 0.15 g/cm$^3$; a plurality of spaced-apart compressed portions formed at least in one surface of said batt, said compressed portions having an average density in the range of from about 0.40 g/cm$^3$ to about 1.00 g/cm$^3$, said compressed portions having a size at said at least one surface in the range of from about 0.0002 cm² to about 0.12 cm²; and said batt having regions defined between said compressed portions, said regions occupying from about 97 percent to about 99.5 percent of the area of said at least one surface of said batt, said regions having an average density that is greater than the average density of said compressed portions, so as to enhance transfer of fluid between adjacent compressed portions while substantially maintaining the absorbency of said batt.

2. The absorbent structure as defined in claim 1 wherein said loose assemblage of fibers includes cellulosic fibers and hydrogen bonds are formed at said compressed portions.

3. The absorbent structure as defined in claim 1 wherein said compressed portions and said regions are formed on both surfaces of said batt.

4. The absorbent structure as defined in claim 1 wherein said batt includes superabsorbent materials to enhance the absorbent capacity thereof.

5. The absorbent structure as defined in claim 1 wherein said batt includes thermoplastic fibers and fusion bonds are formed at said compressed portions.

6. The absorbent structure as defined in claim 1 wherein said compressed areas are generally rectangular in shape.

7. The absorbent structure as defined in claim 1 wherein said compressed portions are formed in a discrete pattern.

8. The absorbent structure as defined in claim 2 wherein the compressed portions are formed on at least one surface of the batt by a toothed roller rolled in the machine direction of the batt and the compressed portions formed on the other surface of the batt are formed by a toothed roller rolled in the cross-machine direction of the batt.

9. The absorbent structure as defined in claim 2 wherein the compressed portions ar formed on at least one surface of the batt by application of ultrasonic energy to discrete areas of the surface.

10. A method of making an absorbent structure having improved fluid transport and fluid distribution characteristics, comprising the steps of: forming a batt having opposing surfaces from a loose assemblage of fibers including cellulosic fibers, said batt having an average initial density of from about 0.03 g/cm³ to about 0.15 g/cm³; and applying pressure to said at least one surface of the batt to define a plurality of substantially uniformly spaced-apart compressed portions and regions between said compressed portions, said compressed portions having an average density in the range of from about 0.40 g/cm³ to about 1.00 g/cm³, said compressed portions having a size in the range of from about 0.0002 cm² to about 0.12 cm², said regions occupying from about 97 percent to about 99.5 percent of the area of said at least one surface of said batt, said regions having an average density that is greater than the average initial density of said batt and less than the average density of said compressed portions, so as to enhance transfer of fluid between adjacent compressed portions while substantially maintaining the absorbency of the batt.

11. The method as defined in claim 10 further including the step of applying an aqueous solution onto said at least one surface of the batt prior to applying pressure thereto so as to form hydrogen-bonded compressed portions.

12. The method as defined in claim 10 wherein pressure is applied to both surfaces of the batt to form compressed portions and regions between the compressed portions on both surfaces of the batt.

13. The method as defined in claim 10 wherein the pressure is applied to the batt by passing a toothed roller over the at least one surface of the batt.

14. The method as defined in claim 12 wherein the pressure is applied to both surfaces of the batt by passing a toothed roller over both of the surfaces of the batt.

15. The method as defined in claim 14 wherein a toothed roller is passed over one of the surfaces of the batt in the machine direction and a toothed roller is passed over the other surface of the batt in the cross-machine direction.

16. The method as defined in claim 10 wherein the batt includes superabsorbent materials to enhance the absorbent capacity thereof.

17. The method as defined in claim 10 wherein said batt includes thermoplastic fibers and fusion bonds are formed at the compressed portions.

18. The absorbent structure as defined in claim 1 wherein said batt has an initial average density in the range of from about 0.05 g/cm³ to about 0.10 g/cm³.

19. The method as defined in claim 10 wherein said batt has an initial average density in the range of from about 0.40 g/cm³ to about 1.00 g/cm³.

20. The method as defined in claim 11 wherein the compressed portions are formed on at least one surface of the batt by application of ultrasonic energy to discrete areas of the surface.

21. The method as defined in claim 20 wherein the ultrasonic energy is applied to the batt as it is passed through a gap between an ultrasonic horn and a cylinder with a pattern of protruding pins.

22. The method as defined in claim 21 wherein the gap between the ultrasonic horn and the outer surface of the cylinder is set so as to contact the batt and facilitate ultrasonic energy transfer into the batt.

23. The method as defined in claim 22 wherein the batt is passed through the gap between the ultrasonic horn and the cylinder a second time to obtain superimposition of a pattern of compressed portions.

24. The method as defined claim 22 wherein the batt is reversed and passed through the gap between the ultrasonic horn and the cylinder a second time to form compressed portions and regions on the other surface of the batt.

* * * * *